United States Patent [19]

Koizumi et al.

[11] Patent Number: 4,460,273
[45] Date of Patent: Jul. 17, 1984

[54] TEST APPARATUS FOR DEFECTS OF PLATE

[75] Inventors: Mitsuyoshi Koizumi; Nobuyuki Akiyama; Yoshimasa Ohshima, all of Yokohama, Japan

[73] Assignee: Hitachi, Ltd., Tokyo, Japan

[21] Appl. No.: 309,485

[22] Filed: Oct. 7, 1981

[30] Foreign Application Priority Data

Oct. 9, 1980 [JP] Japan ................... 55-140609

[51] Int. Cl.³ .............................. G01N 21/88
[52] U.S. Cl. .................... 356/237; 356/239; 250/563
[58] Field of Search ............ 356/237, 239, 430, 431; 250/572, 574, 562, 563

[56] References Cited

U.S. PATENT DOCUMENTS

| | | | |
|---|---|---|---|
| 3,536,405 | 10/1970 | Flower | 250/572 |
| 3,536,409 | 10/1970 | Flower | 250/572 |
| 3,836,261 | 9/1974 | Clarke | 356/237 |
| 3,972,616 | 8/1976 | Minami et al. | 356/239 |
| 4,030,830 | 6/1977 | Holly | 356/237 |
| 4,148,065 | 4/1979 | Nakagawa | 250/563 |

Primary Examiner—Vincent P. McGraw
Assistant Examiner—L. A. Dietert
Attorney, Agent, or Firm—Antonelli, Terry & Wands

[57] ABSTRACT

A test apparatus for detecting defects on a plate is disclosed. An illumination light is focused to one surface of the plate and another illumination light is focused to the other surface of the plate, and scattered light from the defects on the surfaces are detected to separately detect the defects on the front and rear surfaces of the plate.

15 Claims, 42 Drawing Figures

FIG. 10
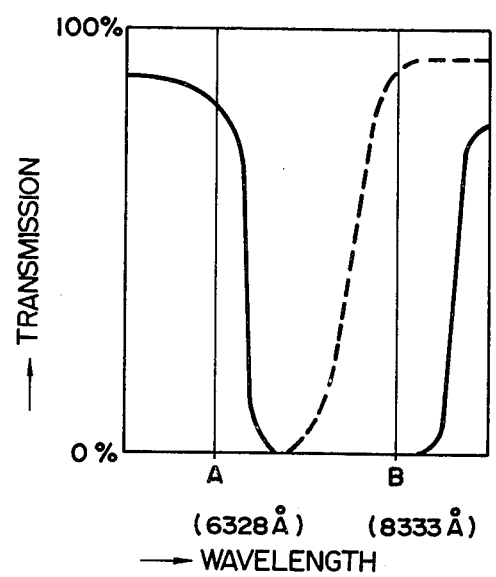
FIG. 11
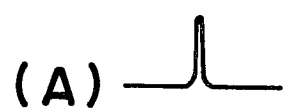

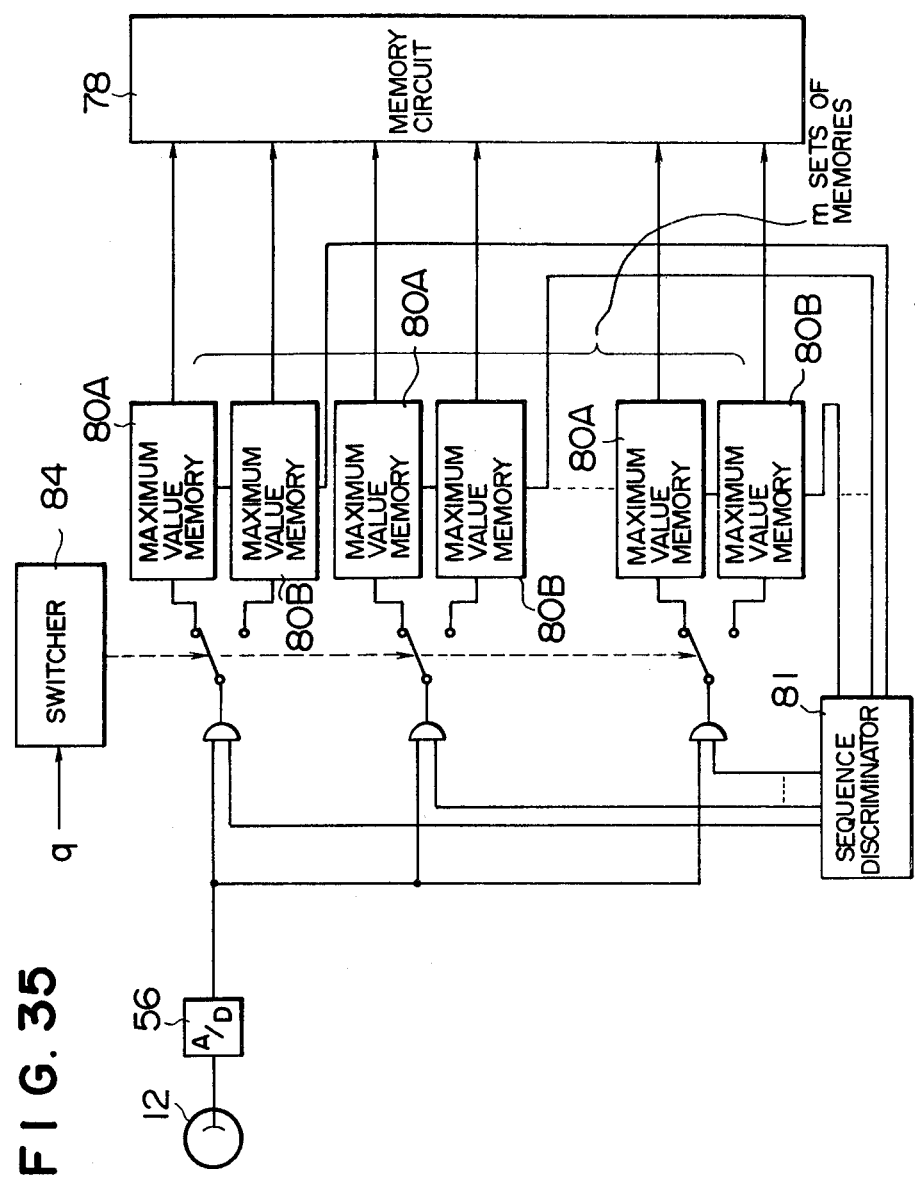
F I G. 35

TEST APPARATUS FOR DEFECTS OF PLATE

The present invention relates to a test apparatus for defects of a plate such as a glass plate of an image pickup tube, a photomask for LSI and a wafer or a magnetic bubble memory.

In the test of the defects (such as minute unevenness, foreign materials and cracks) on a surface of a transparent glass plate, particularly of the image pickup tube glass plate, the LSI photomask and the magnetic bubble memory wafer (garnet crystal), it is necessary to distinguish a front side and a rear side of the transparent plate before it is tested for the surface defects.

As shown in FIG. 1, the image pickup tube 3 includes a glass plate 1 having a thickness of 1.5–2.05 mm and a diameter of 15–30 mm and a photo-conductive layer 2 evaporated on one side (side B) of the glass plate 1. Since the side B is scanned by an electron beam 3a, defects on the surface B appear as white spot defects on a screen. Accordingly, in the test for the defects on the surface B, a spot-like unevenness in the order of 0.1 $\mu$m in size must be detected. A defect on a surface A may be permitted up to the unevenness of 10 $\mu$m because an incident light is defocused as much as the thickness of the glass.

FIG. 2 shows a method for exposing a photo-mask chromium pattern on a Si-wafer 5. A photo-mask 4 is placed on a photo-resist 5a on the Si wafer 5 in contact thereto and the chromium pattern 4b is exposed exactly onto the photo-resist 5a by an exposing light 4c. A defect of a size in the range of 1–2 $\mu$m on the chromium pattern 4b of the photo-mask 4 results in a defective wafer. On the other hand, a defect on an upper surface of the photo-mask 4 is permitted up to 10 $\mu$m because the incident light is defocused as much as the thickness of the glass. Accordingly, in the test for the defects on the unpatterned glass prior to the evaporation of the chromium pattern, a defect in the order of 1–2 $\mu$m must be detected for one surface while a defect in the order of 10 $\mu$m must be detected for the other surface.

A GdGa garnet (GGG) substrate which is used as a magnetic bubble memory wafer material is also tested for surface defects because a pattern having a 1 $\mu$m width is evaporated thereon to generate and erase magnetic bubbles. However, the defects (cracks or unevenness) on the rear surface of the substrate may be permitted.

FIG. 3 shows a configuration of a prior art defect test apparatus. A laser beam 7a is focused onto a surface of a sample 6 by an object lens 7. If there is no defect on front and rear surfaces of the sample 6, the laser beam 7a is transmitted upwardly straightforward, but if there is a defect, the laser beam 7a is scatterd toward a condensing lens 8. If a pinhole plate 9 is arranged to detect the defect on an upper surface 6a of the sample 6, the scattered light due to the defect on a lower surface 6b is interrupted by the pinhole plate 9. A photo-multiplier 9 arranged behind the pinhole plate 9 detects the scattered light transmitted through the pinhole.

When the thickness of the sample is sufficiently large, this apparatus can detect only the defect on the desired surface by the isolation function of the pinhole 9. However, when the thickness of the sample is small or the light is scattered (10a in FIG. 4) by a defect on the surface, other than the desired surface the detection is affected since the pinhole cannot provide effective isolation function.

It is an object of the present invention to provide a defect test apparatus for a transparent plate which has an improved detection and isolation function for the defects on front and rear surfaces.

In order to achieve the above object, in accordance with an aspect of the present invention, two illumination lights (such as laser beams) are focused to the front and rear surfaces and outputs of photo-multipliers which detect the respective illumination lights are compared to discriminate the surface on which a defect exists by making use of the fact that a scattered light from the matched focused laser beams is more intensive than a scattered light from the mismatched focused laser beams.

In accordance with another aspect of the present invention, a maximum value memory circuit is provided which, when a signal larger than a threshold is applied in one scan period, produces a gate signal of a predetermined duration centered at the position on a scan line in the succeeding scan period until the input signal falls below the threshold, and compares peak values of the input signal in each scan period and stores the maximum one of them and the corresponding position and detection means which determines the presence of one defect each time when the maximum value memory circuit stores one maximum value and the corresponding position and the magnitude and the position of the defect by the stored maximum value and the corresponding position so that each defect is detected as one defect even if it is large to allow the detection of the exact number of defects or deposits.

According to a further aspect of the present invention, when the plate is transparent, the plate is alternately scanned by two beams focused to front and rear surfaces of the plate and the resulting signals are processed by separate maximum value memory circuits to determine the respective maximum values, and the surface which presents the larger maximum value is determined to have a defect represented by the larger maximum value and the corresponding position in order to discriminate the front or rear surface of the transparent plate on which the defect or deposit exists.

In the drawings:

FIG. 10 shows transmissions of a dichromatic mirror and a color filter used in the double wavelength system;

FIG. 11 shows an output detected in the double wavelength system;

FIGS. 15A to 15C show a structure of a filtered plate for a single-tube color camera in which FIG. 15A is a plan view, FIG. 15B is a front view and FIG. 15C shows steps of the filter;

FIGS. 16A and 16B illustrate an arrangement for condensing a light while eliminating scattered light from the steps of the filter, in which FIG. 16A is a plan view and FIG. 16B shows a side view;

FIGS. 17A and 17B show an arrangement for condensing a light by an ellipsoidal condensing mirror, in which FIG. 17A shows a front view and FIG. 17B shows a sectional view taken along a line XVIIB—XVIIB in FIG. 17A;

FIG. 35 shows a block diagram of a test apparatus for defects on a plate having m maximum value memory circuits.

The preferred embodiments of the present invention will now be specifically explained with reference to the accompanying drawings.

Figure 1:
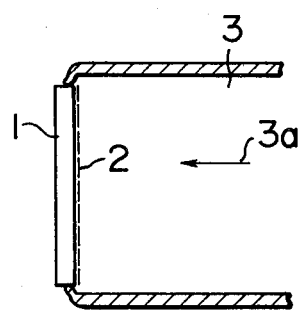
FIG. 1 shows a structure of an image pickup tube.
Figure 2:
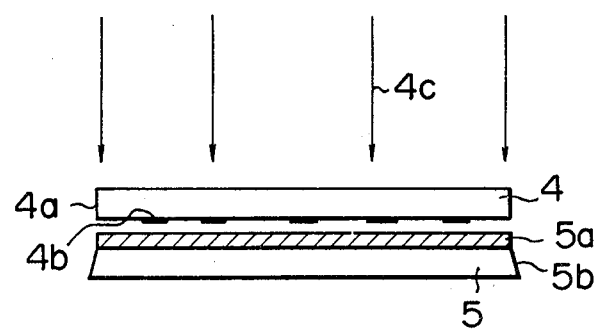
FIG. 2 illustrates light exposure of a photo-mask to a wafer.
Figure 3:
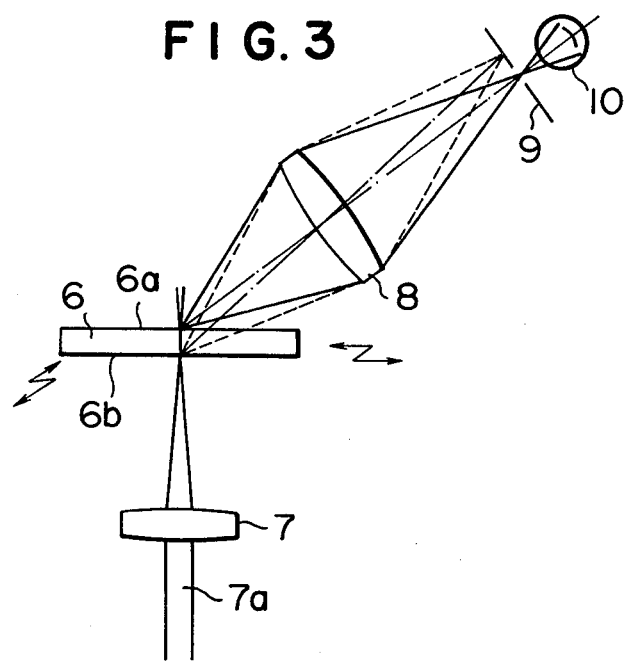
FIG. 3 shows a schematic configuration of a prior art glass plate test apparatus.
Figure 4:
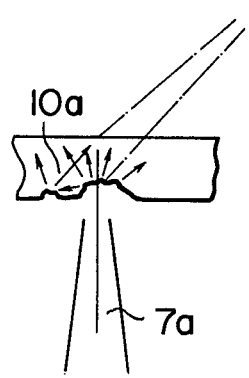
FIG. 4 shows a scattered light from a sample.
Figure 5:
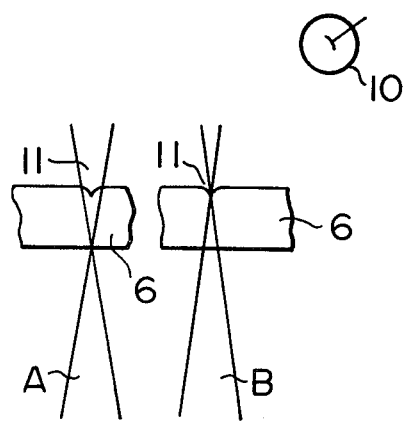
FIG. 5 illustrates a principle of the present invention.
Figure 6:
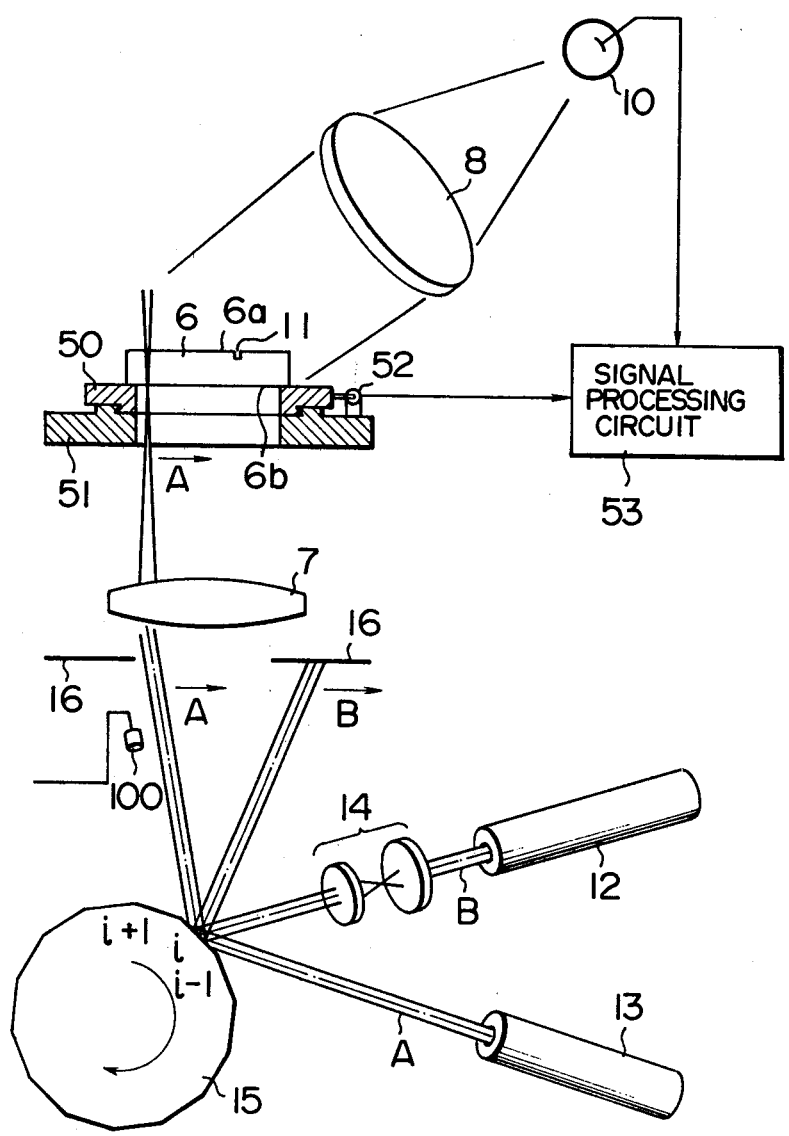
FIG. 6 illustrates a time-division system in accordance with one embodiment of the transparent plate defect test apparatus of the present invention.

(1) Time Division System (FIG. 6)

Figure 7:
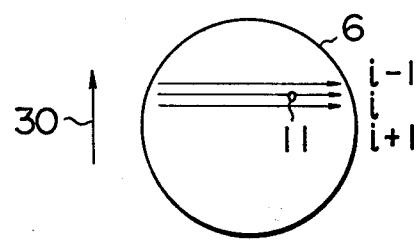
FIG. 7 illustrates laser beam scan.
Figure 8:
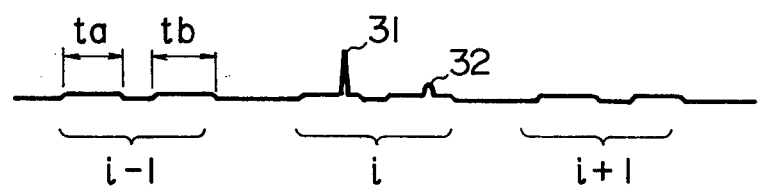
FIG. 8 shows an output detected in the scan shown in FIG. 7.

FIG. 6 shows an embodiment in which two He-He laser beams are used as illumination lights. The laser beam A emanated from a laser oscillator 13 is focused onto a lower surface 6b of a sample 6 and the laser beam B emanated from a laser oscillator 12 is focused onto an upper surface 6a of the sample 6. Thus, by detecting an output of a photo-electric tube 10, defects on the upper and lower surfaces of the sample can be discriminated. A focusing point adjuster 14 including two convex lenses is arranged for the laser beam B to deviate the focusing point of the laser beam B from the focusing point of the laser beam A. The laser beams are both directed to a reflection plane i of a rotating polygonal mirror 15. As the reflection plane i rotates, the scan positions are moved as shown by arrows A and B. A stop 16 is arranged below a condensing lens 7 to restrict the scan range. The construction is such that the laser beams A and B do not simultaneously scan the sample 6. Since the sample 6 is continuously moved normally to a plane of the drawing, the entire surface of the sample 6 is scanned by the laser beams A and B, as shown in FIG. 7. FIG. 8 shows a detection output for a defect 11 on the upper surface, in which $t_a$ and $t_b$ show times at which the sample 6 is scanned by the laser beams A and B, and they correspond to an aperture of the stop 16. As the sample 6 is moved, reflection planes $i-1$, i and $i+1$ sequentially scan the sample 6 so that the defect 11 is detected by the scan of the reflection plane i. A detection output 31 by the laser beam B is larger than a detection output 32 by the laser beam A so that it is determined that the defect 11 is on the upper surface.

Figure 9:
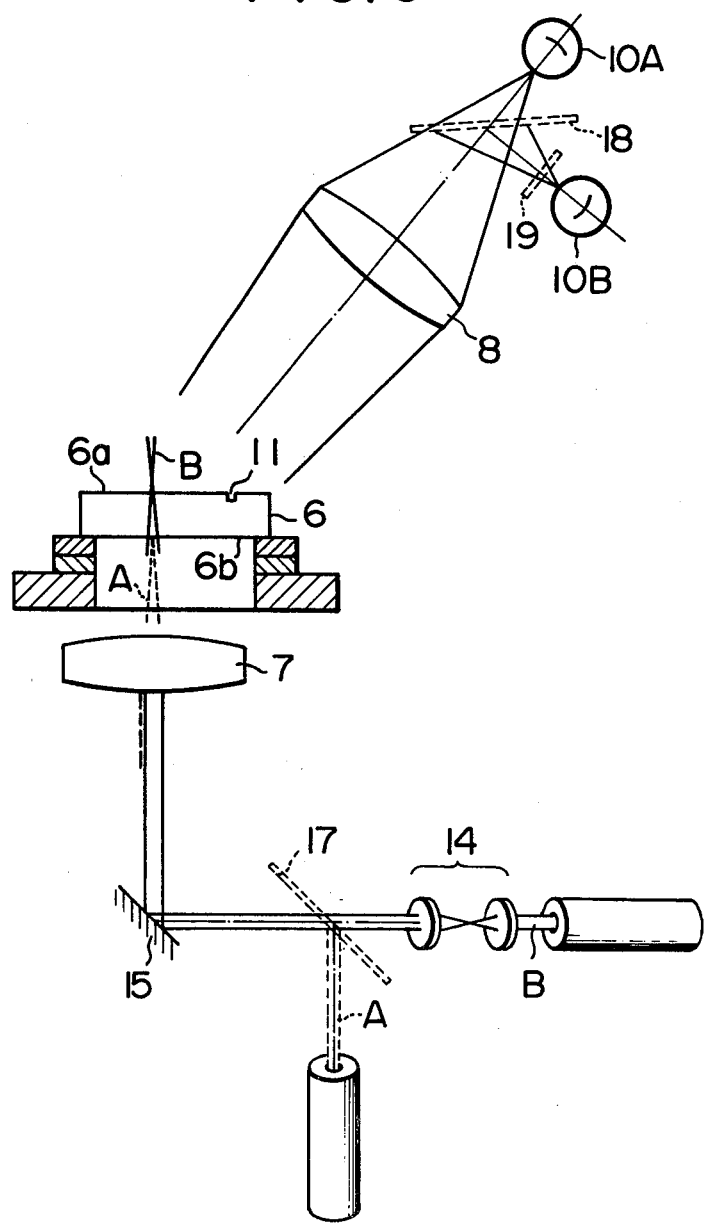
FIG. 9 shows a double wavelength system in accordance with another embodiment of the transparent plate defect test apparatus of the present invention.

(2) Double Wavelength System (FIG. 9)

FIG. 9 shows a system which uses laser beams A and B of different wavelengths (e.g., the laser beam A is emanated from a 6328 Å He-He laser and the laser B is emanated from a 8333 Å semiconductor laser). The laser beam A is reflected by a silver-mirror 17 and the laser beams A and B simultaneously scan the sample 6. The laser beams A and B are focused to the lower surface 6b and the upper surface 6a, respectively, of the sample 6. Scattered lights condensed by a condensing lens 8 are divided into two optical paths by a dichromatic mirror 18 and a photo-electric tube 10A detects the scattered light from the laser beam A while a photo-electric tube 10B detects the scattered light from the laser beam B. FIG. 10 shows a transmission of the dichromatic mirror 18. Since the laser beam B (8333 Å) does not transmit through the dichromatic mirror 18, the photo-electric tube 10A detects only the laser beam A (6328 Å). A reflected light from the dichromatic mirror 18 includes both the laser beam B (8333 Å) and the laser beam A (6328 Å) but since the laser beam A (6328 Å) is cut off by a color filter 19, the photo-electric tube 10B detects only the laser beam B (8333 Å). FIG. 11 shows detection output for the defect 11 on the upper surface 6a of the sample 6, in which (A) shows the output from the photo-electric tube 10B and (B) shows the output from the photo-electric tube 10A. When the intensities of the laser beams A and B are different or the sensitivities of the photo-electric tubes 10A and 10B are different, ND filters may be used to equalize the intensities of the laser beams A and B or the gains of the photo-electric tubes 10A and 10B may be varied to equalize the output sensitivities of the photo-electric tubes 10A and 10B.

When the plate comprises a plurality of layers bonded by transparent bond and the defects on the respective layer should be detected, the number of laser beams is increased to the number of layers.

In the defect test, a size of the defect is to be detected in a certain application. A linearity between the scattered light output and the size of the defect is restricted by a diameter of the illuminating laser beam. When a large diameter of laser beam is used to maintain the linearity, a small defect cannot be detected.

Figure 12:
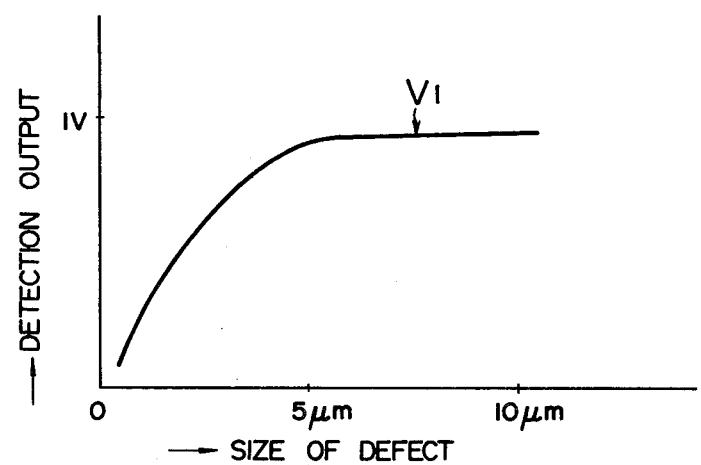
FIG. 12 shows a detection output $V_1$ versus a defect size when the defect on a Si-wafer is tested by a laser beam of 2 $\mu$m in diameter.
Figure 13:
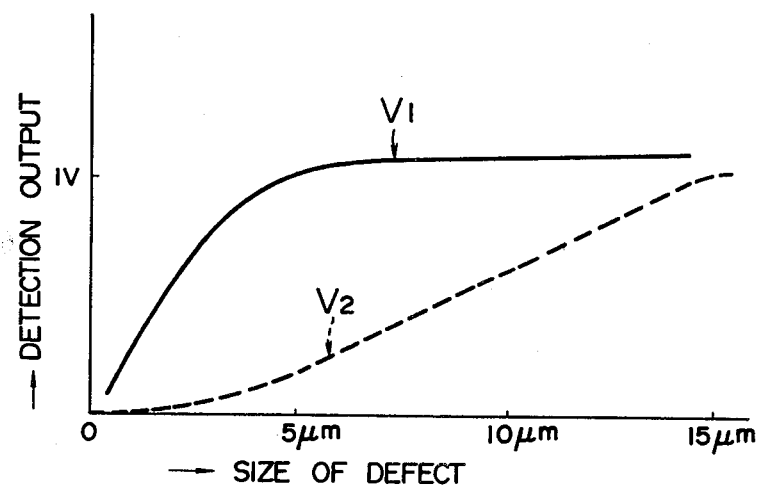
FIG. 13 shows a detection output $V_2$ versus a defect size when the defect on the Si-wafer is tested by laser beams of 2 μm and 10 μm in diameter.
Figure 14:
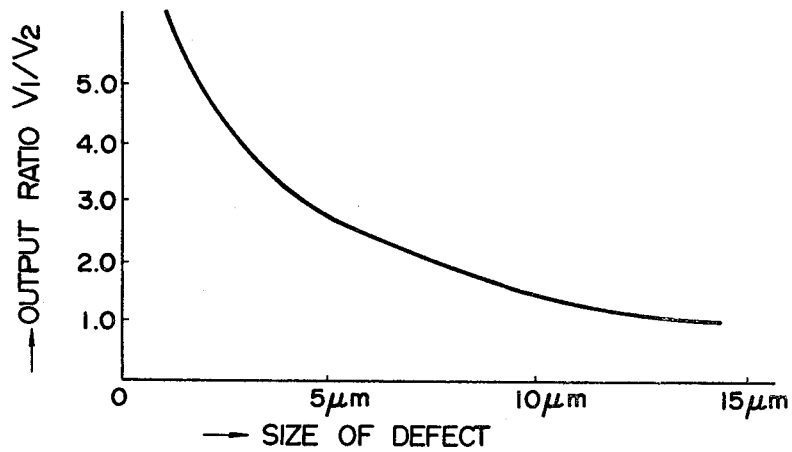
FIG. 14 shows a characteristic of an output ratio of the detection output $V_1$ shown in FIG. 12 to the detection output $V_2$ shown in FIG. 13.

The detection of a defect on a Si-wafer is now explained. FIG. 12 shows a detection output for the defect on the Si-wafer by a laser beam of 2 μm in diameter. The detection output $V_1$ is linear when the size of the defect is smaller than 5 μm but the linearity is lost when the size of the defect is larger and the size of the defect cannot be determined. FIG. 13 shows a detection output $V_2$ when a laser beam of 10 μm in diameter is used. While it cannot detect the defect smaller than 2 μm, it maintains the linearity for the defect of up to 15 μm. By taking a ratio ($V_1/V_2$) of the detection outputs for the 2 μm laser beam and the 10 μm laser beam, the detection output is linear over a wide range as shown in FIG. 14. In the illustrated example, it is determined that the defect is a small defect smaller than 2 μm if the output ratio $V_1/V_2$ is larger than 5, an intermediate defect between 2-7 μm when the output ratio $V_1/V_2$ is between 2 and 5, and a large defect larger than 7 μm when the output ratio $V_1/V_2$ is smaller than 2.

Figure 15A:
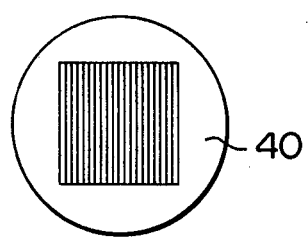
Figure 15B:
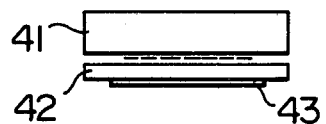
Figure 15C:
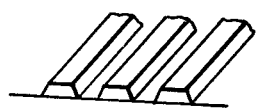

Referring to FIGS. 15A to 15C, a plate 40 with a filter for a single-tube color camera is explained. It comprises a glass substrate 41 of 2.5 mm thick having a color analying organic filter evaporated thereon in a stripe pattern as shown in FIG. 15C, and a thin glass plate 42 of 30 μm thickness is bonded thereto by bonding material (7 μm thick). Since a photo-conductive layer 43 is applied on the surface of the thin glass plate 42, a defect as small as 0.1 μm on the surface must be detected although a defect as large as 10 μm in the bonding layer may be permitted. In the prior art system, such a test has not been attained because of the affect by the scattered light from the steps of the filter pattern.

Figure 16A:
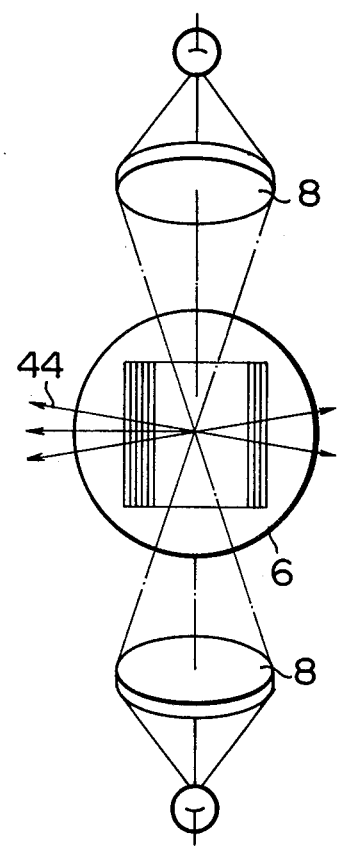
Figure 16B:
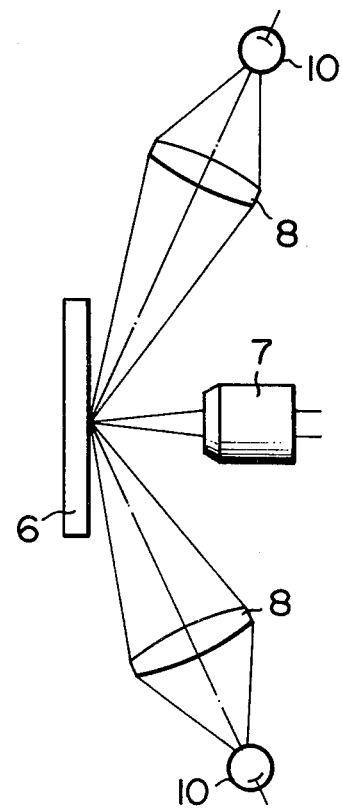
Figure 17A:
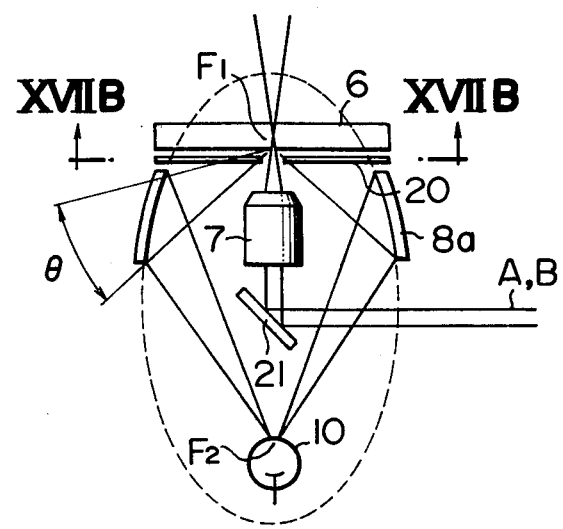
Figure 17B:
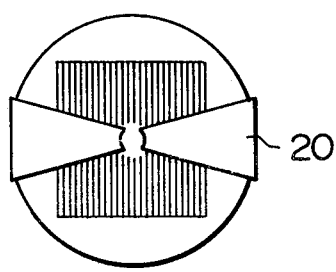

By utilizing the fact that the direction of the scattered light from the filter pattern is constant, the defect can be detected. FIGS. 16A and 16B show an embodiment in which two condensing systems are arranged to avoid the scattered light 44 from the steps of the filter pattern. FIG. 17 shows an embodiment in which an ellipsoidal condensing mirror 8a for effectively condensing a wide range of scattered light is used. Focal points $F_1$ and $F_2$ of the condensing mirror 8a correspond to a sample detection point and a position of the photo-electric tube 10, and the scattered light at the detection point is condensed in a ring pattern within an angle θ and directed to the photo-electric tube 10. The scattered light from the filter pattern is interrupted by a light stopper 20.

Figure 18:
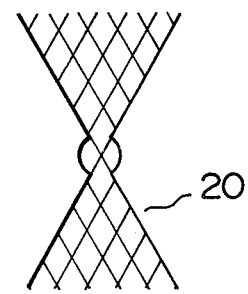
FIG. 18 shows an arrangement of a light stopper used to test a diameter filter pattern.

FIG. 18 shows a diamond filter pattern light stopper. By using the ellipsoidal condensing mirror 8a, the light stopper 20 and the pair of laser beams A and B focused to the photo-conductive layer and the bonding layer, respectively, a defect larger than 0.1 μm on the photo-conductive layer and a defect larger than 10 μm on the bonding layer can be discriminatively detected. A N.A. of the object lens 7 is 0.4, the diameter of the laser beam is 2 μm (focused) and 20 μm (defocused by 30 μm). Since the laser beam is fully expanded on the upper surface of the glass substrate 2.5 mm thick, a defect even 100 μm does not affect to the detection outputs from the photo-conductive layer and the bonding layer.

Referring now to FIGS. 19 to 35, defect test procedure will be explained in detail. As shown in FIG. 6, the sample 6 is fixed on a movable table 50 which is moved by a motor (not shown) and a lead screw (not shown) in a direction normal to the plane of FIG. 6. The position is detected by a sensor 52 connected to the movable table 6.

The laser beams from the laser tubes 12 and 13 are deflected by the rotation of the rotating mirror 15 and scan the surface of the sample 6 through the lens 7. If no defect is present on the surface of the sample 6, the illuminated laser beams pass upward. If any defect is present, a scattered light is formed and a portion of the scattered light is condensed by the condensing lens 18, the condensed light is detected by the photo-electric detector 10, and the detected signal is processed by a signal processing circuit 53 to be described later. The light stopper 16 is arranged to limit the scan range of the laser beam on the sample 6 and a timing sensor 100 detects a left end of scan or a start point of scan by the laser beam.

Figure 19:
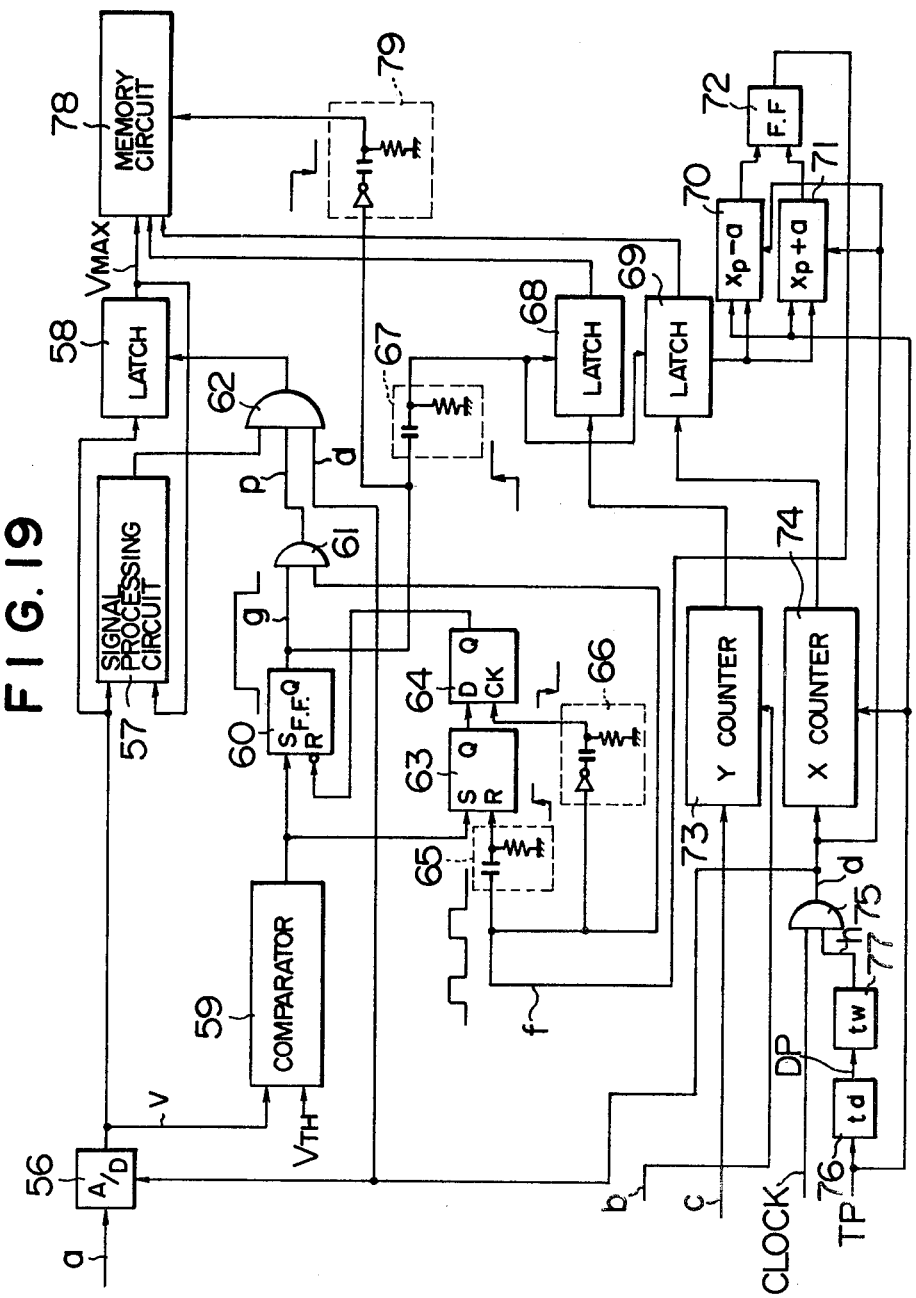
FIG. 19 shows an embodiment of a maximum value memory circuit which is a feature of the present invention.

FIG. 19 shows an embodiment of the maximum value memory circuit which is a principal part of the signal processing circuit 53. The maximum value memory circuit continues to produce a gate signal over a certain number of scan periods when a defect is present. It has a function of producing a two-dimensional frame and a function of determining and storing a maximum input signal within a frame.

Figure 20:
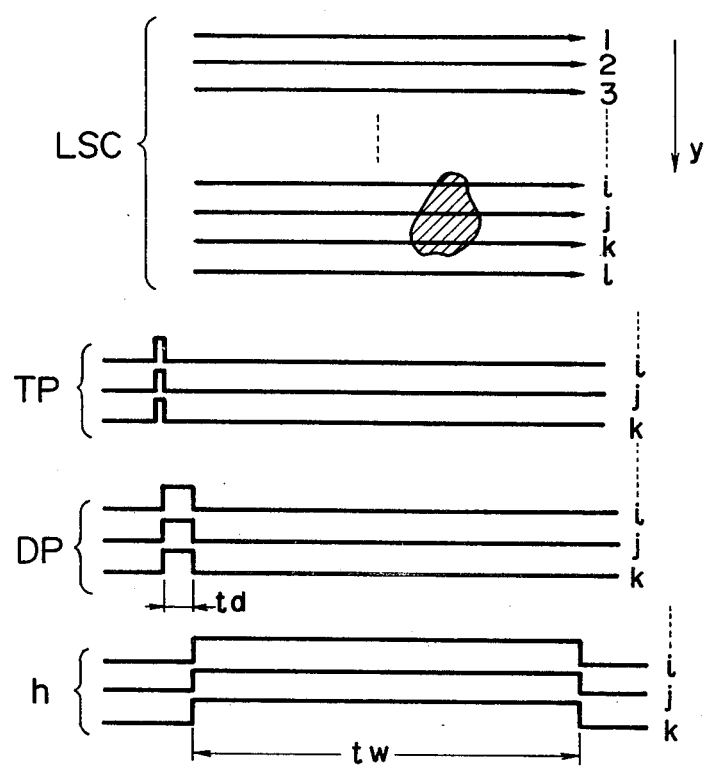
FIG. 20 shows a time chart for the generation of a test gate signal.

Referring to FIG. 19, the generation of a test gate signal h is explained with reference to a time chart shown in FIG. 20. A timing pulse TP is applied at the beginning of each scan line as shown in FIG. 20 and it is produced by the timing sensor 100 shown in FIG. 6. A delayed pulse DP having a duration $t_d$ is produced by a delay circuit 76 in synchronism with the fall of the timing pulse TP, and the test gate pulse h having a duration $t_w$ is produced by a gate 77 at the fall of the delayed pulse DP, as shown in FIG. 20. The test gate pulse h defines a range of the plate to be tested. Only when the gate pulse h is ON, a clock pulse d is supplied to the circuits through an AND gate 75.

Figure 21:
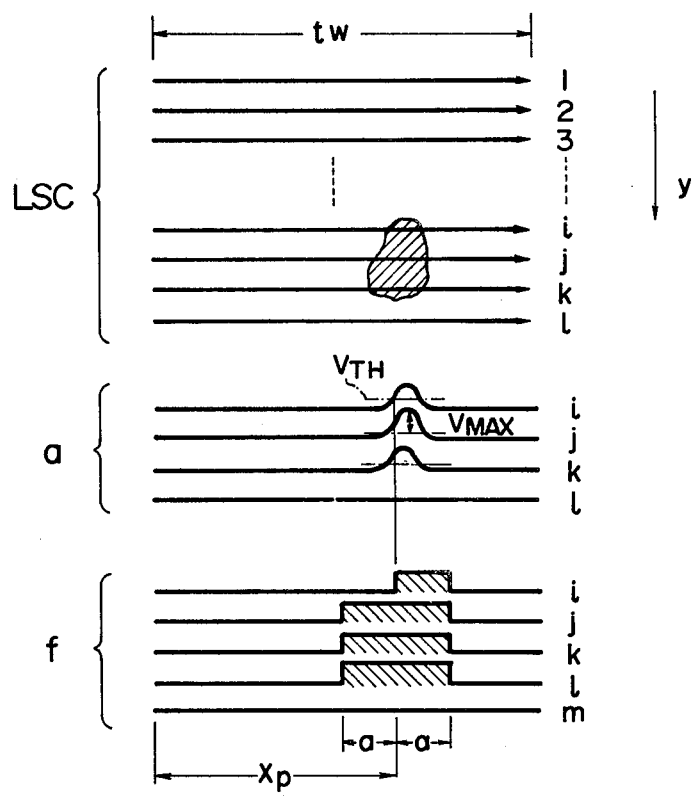
FIG. 21 shows a time chart for the generation of a two-dimensional frame (gate P)
Figure 22:
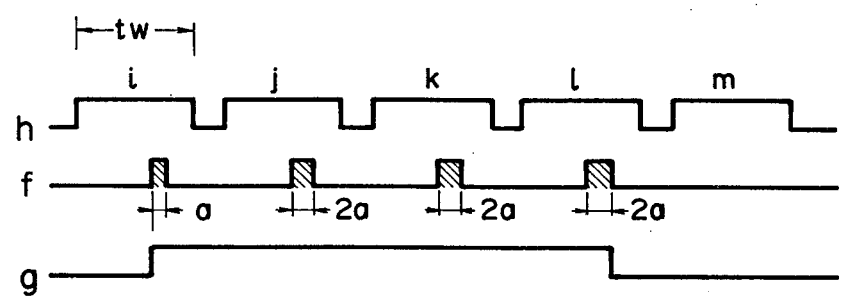
FIG. 22 shows a time chart illustrating a relation between the gates.

The generation of the two-dimensional frame and the storing operation of the maximum value and the position thereof are explained with reference to a time chart shown in FIG. 21. In FIG. 19, an input signal a from the photo-electric detector 10 shown in FIG. 6 is digitized to a signal v by an A/D converter 56 and the signal v is compared with a preset threshold $v_{TH}$ by a compare circuit 59. When the signal v exceeds the threshold $v_{TH}$ at a position $x_p$ on the scan line i shown in FIG. 21, a "1" output of the compare circuit 59 sets a flip-flop 60 so that a gate signal g is rendered "1". Since a gate signal f is also "1" at this time as will be explained later, a gate signal p at an output of an AND gate 61 is also ON. The signal p is the two-dimensional gate signal. The gate signal p is ON between $x_p$ and $x_p + a$ on the scan line i as shown in FIG. 21 where a is a constant length. On the other hand, the signal v is compared with a previous maximum value $v_{MAX}$ within a period of a gate signal p latched in a latch circuit 58 by the compare circuit 57, and when $v > v_{MAX}$, an output signal of the compare circuit 57 opens an AND gate 62 to update the maximum value $v_{MAX}$ in the latch 58. In this manner, the latch 58 always latches the previous maximum value $v_{MAX}$ within the period of the gate signal p.

The fall of the gate signal g is supplied to latches 68 and 69 through a differentiation circuit 67. Thus, a Y address i which is a content of a Y counter 73 which is set by a start pulse b indicating a start of scan and counts up an output c of the sensor 52 shown in FIG. 6 and an X address $x_p$ which is a content of an X counter 74 which is reset by the timing pulse TP produced at the beginning of each scan line and counts up the clock pulse d are latched to the latches 68 and 69, respectively.

The X address $x_p$ latched in the latch 69 is supplied to arithmetic circuits 70 and 71 where $x_p-a$ and $x_p+a$ are calculated, respectively, where a is the constant. A flip-flop 72 is set and reset at the times when the number of timing pulses TP reaches $x_p-a$ and $x_p+a$, respectively. In this manner, a gate signal f shown in FIG. 21 is produced for scan lines j, k and l.

During the scan lines j and k and a first portion of the scan line l, the gate signal g remains ON (as shown in a time chart shown in FIG. 22), and since the gate pulse p assumes the same state during this period the maximum value of the signal v is updated as required and the updated maximum value and the corresponding position are stored in the latch 58. In the scan line l, since $v<v_{TH}$ in the example shown in FIG. 21, the gate signal g is turned off at the position $x_p+a$ and the two-dimensional frame is terminated.

Figure 23:
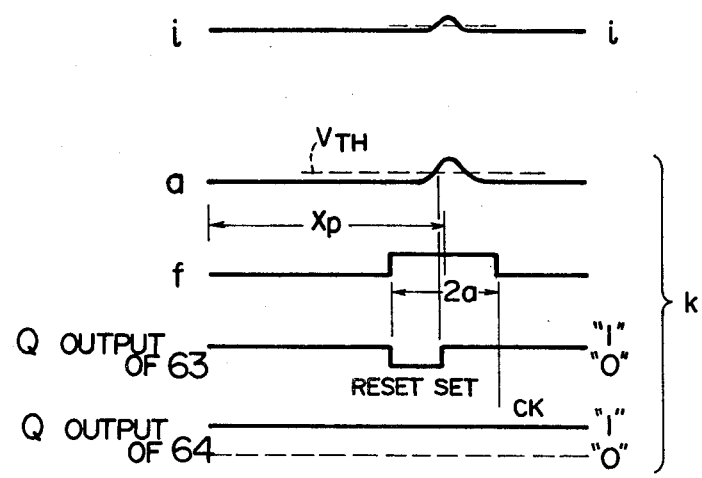
FIGS. 23 and 24 show time charts for illustrating a two-dimensional frame gate termination operation.
Figure 24:
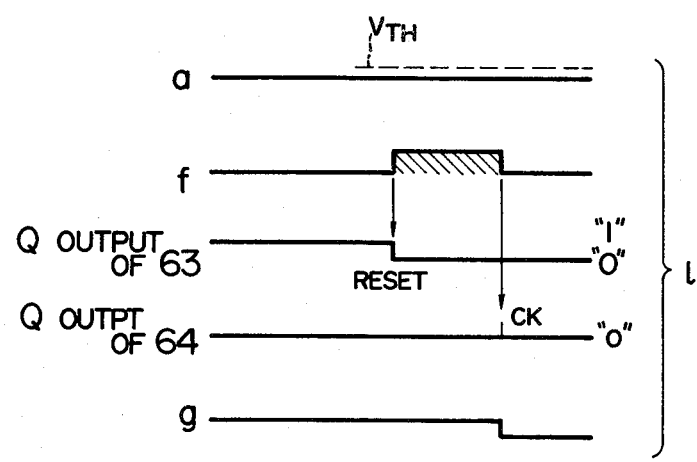
Figure 25:
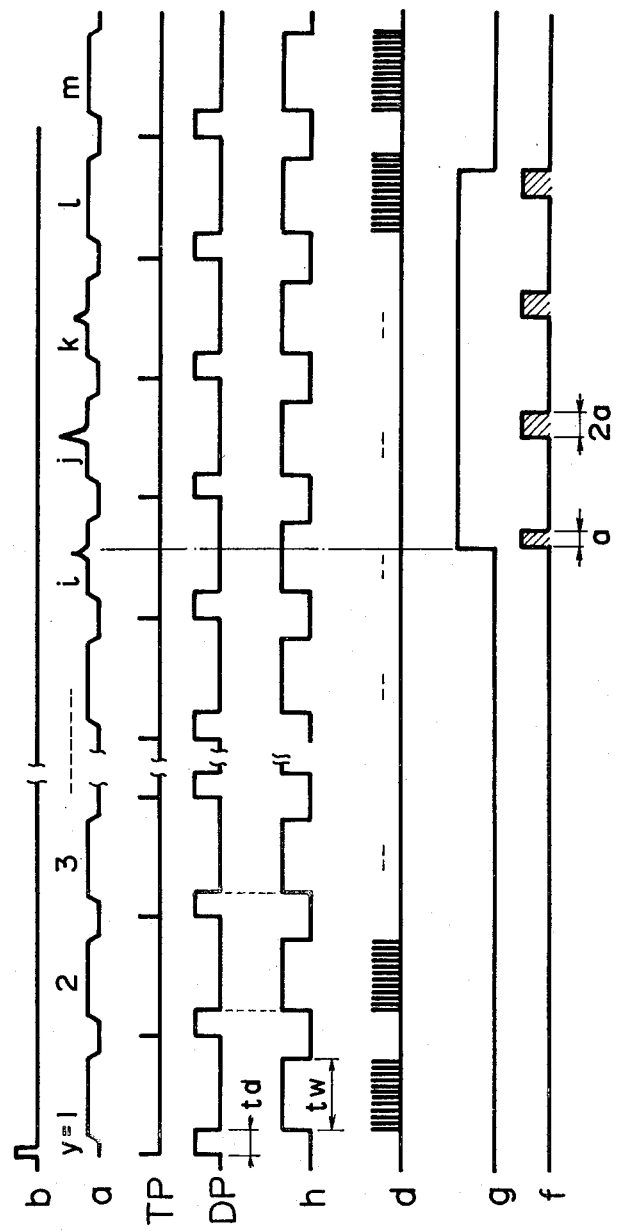
FIG. 25 shows a time chart for signals illustrating an overall operation of the circuit of FIG. 19.

FIGS. 23 and 24 show time charts for illustrating the above operation. The rise of the gate signal f ($x=x_p-a$) is detected by a differentiation circuit 65 to reset a flip-flop 63. When $v>v_{TH}$ as is the case for the scan line k, the flip-flop 63 is set when the output of the compare circuit 59 assumes "1". On the other hand, at the fall of the gate signal f ($x=x_p-a$) detected by a differentiation circuit 66, the Q-output of the flip-flop 63 is "1" and a Q-output of a flip-flop 64 is also "1". Accordingly, a flip-flop 60 is not reset. That is, the gate pulse g remains ON. In the scan line l, the condition of $v<v_{TH}$ is met between $x_p-a$ and $x_p+a$ and the Q-output of the flip-flop 63 remains OFF. Accordingly, the Q-output of the flip-flop 64 is "0" when $x=x_p+a$ and the flip-flop 60 is reset so that the gate signal f is turned off at this moment. In this manner, when a defect extends over a plurality of scan lines, the largest signal v in the scan lines and the corresponding position are detected. FIG. 25 shows a time chart of an overall operation described above.

If the constant a which defines the width of the two-dimensional frame is too large, a plurality of defects are detected as one defect, and if it is too small, one defect is detected as two or more defects (as will be explained later). Accordingly, the constant a must be properly set.

When the gate signal g is turned off, the fall thereof is detected by a differentiation circuit 79 and the X and Y coordinates ($x=x_p$, $y=i$) in the latches 68 and 69 which indicate the maximum value $v_{MAX}$ latched in the latch 58 and the corresponding position are supplied to a memory circuit 78. This completes the detection of one defect.

Figure 26A:
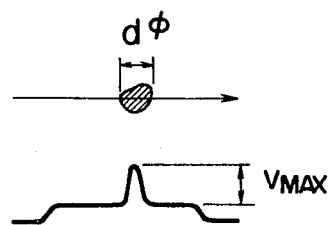
FIGS. 26A and 26B show a measured data for the size of a crack and an output signal.
Figure 26B:
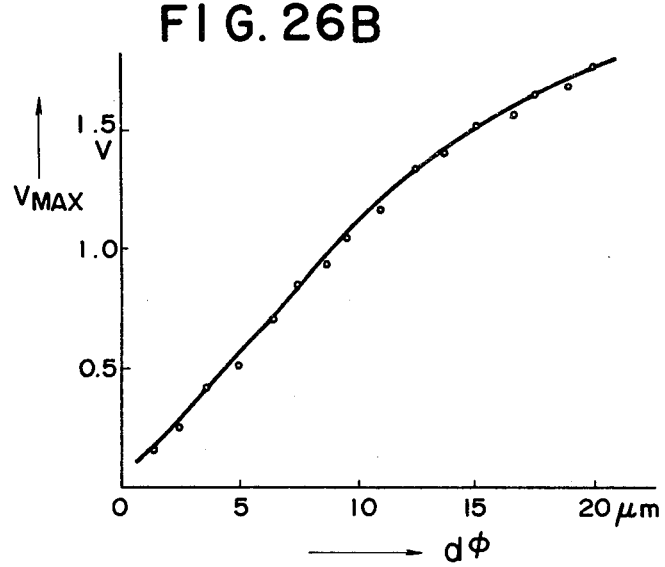

The reason for storing the maximum value $v_{MAX}$ of the signal v is that the size of the defect can be determined by the stored $v_{MAX}$ because the size $d\phi$ (diameter in the scan direction) of the defect is substantially proportional to $v_{MAX}$ as shown in measured data of FIGS. 26A and 26B.

Figure 27:
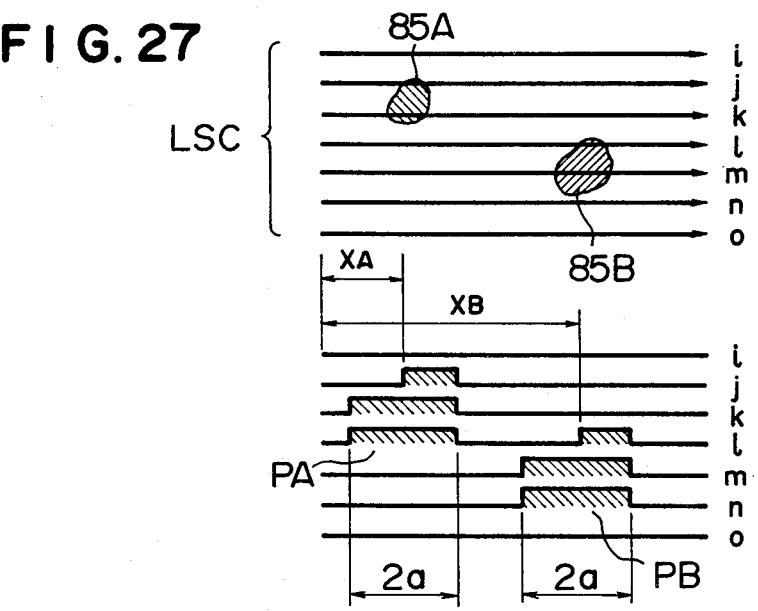
FIGS. 27 to 29 illustrate operations when two defects are included.
Figure 28:
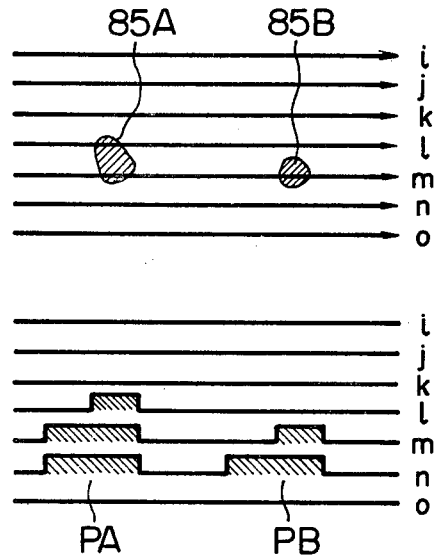
Figure 29:
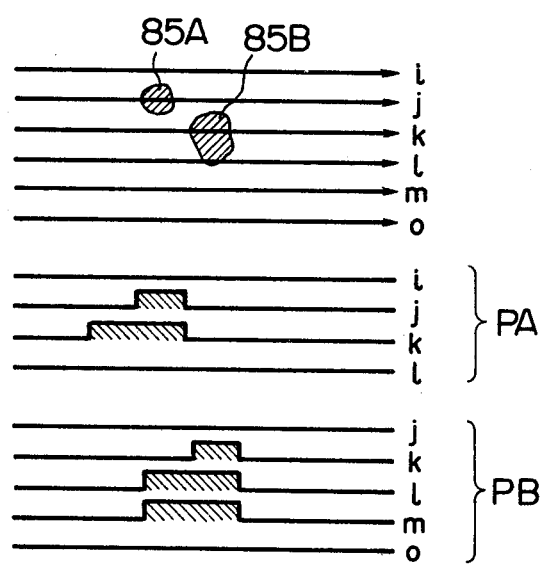

The test procedure where more than one defects (or foreign materials) exist on one test surface is now explained. For the sake of simplification, it is assumed that two defects 85A and 85B exist as shown in FIGS. 27-29. In the case shown in FIG. 27, since a gate pulse PB is generated after a two-dimension gate pulse PA has been terminated, one maximum value memory circuit shown in FIG. 19 is sufficient. However, in the case shown in FIG. 28 or 29, since the gate pulse PB is generated before the gate pulse PA is terminated, two maximum value memory circuits must be arranged in parallel.

Figure 30:
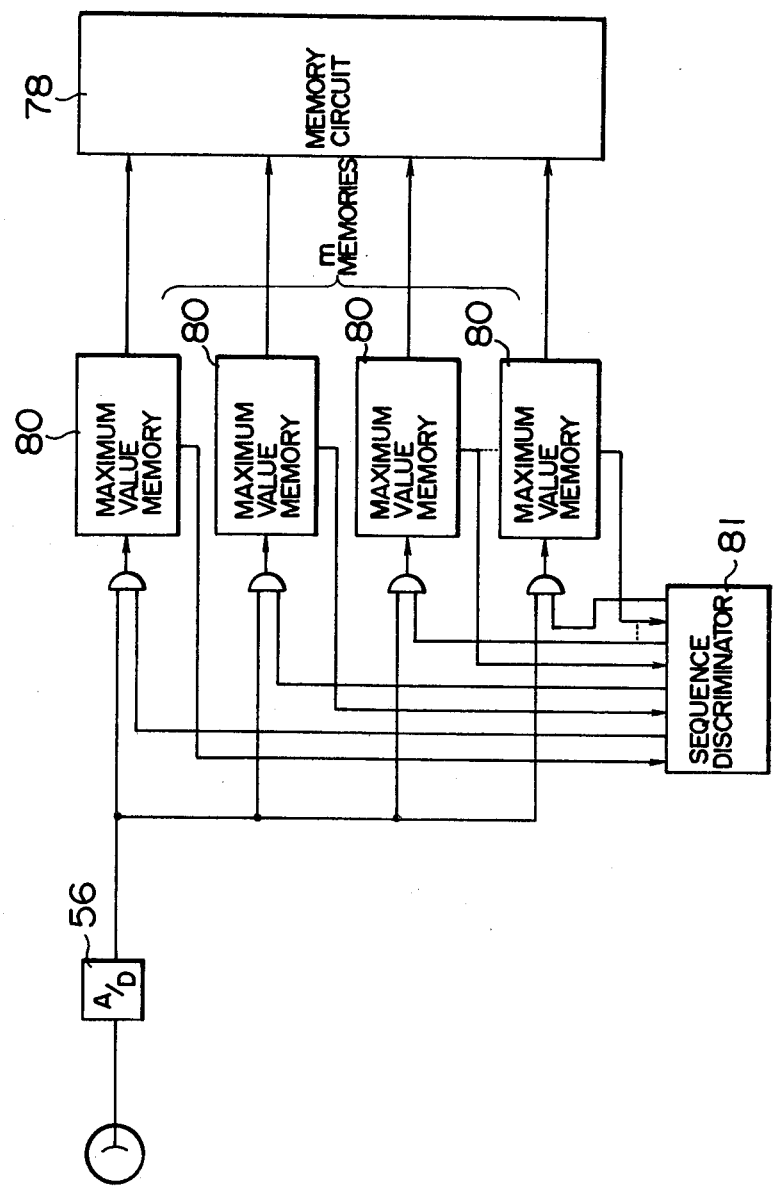
FIG. 30 shows a block diagram of a defect test apparatus having m parallel maximum value memory circuits.

FIG. 30 shows a schematic diagram of a defect test apparatus which can simultaneously detect as much as m defects. Busy or free states of the m maximum value memory circuits 80 are determined by a sequence discriminator 81 and a free memory circuit 80 is allotted to each newly detected defect.

Another embodiment of the test apparatus for the defects on the plate in accordance with the present invention is explained below.

Figure 31:
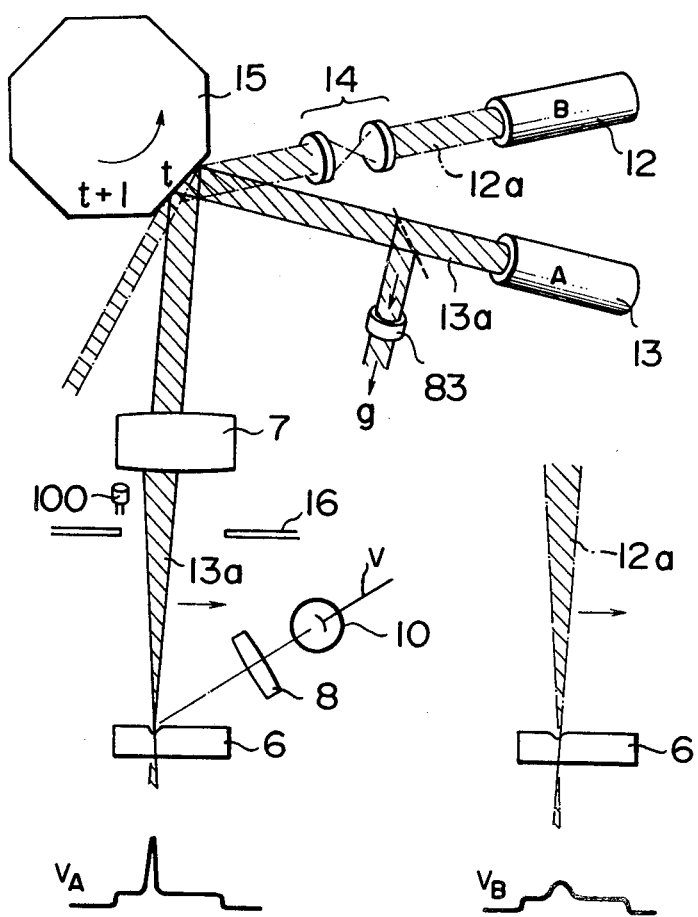
FIG. 31 shows a scanner of a defect test apparatus for detecting defects on front and rear sides of a transparent sample and an output signal resulting from a surface defect.

FIG. 31 illustrates the scan operation in an apparatus for detecting the sizes and the number of defects while discriminating the defects on the front and rear sides of the transparent sample 6 such as a glass plate. A laser beam 13a is focused to the front surface of the sample 6 and a laser beam 12a passed through a beam converter 14 is focused to the rear surface of the sample 6, and they alternately scan the sample 6 as a reflecting plane t of the rotating mirror 15 rotates.

Figure 32A:
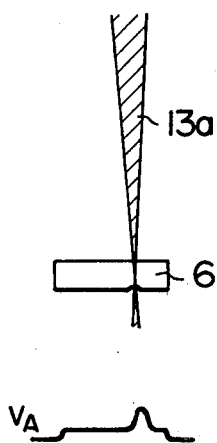
FIGS. 32A and 32B show output signals due to a defect on a rear surface when scanned by the scanner of FIG. 31.
Figure 32B:
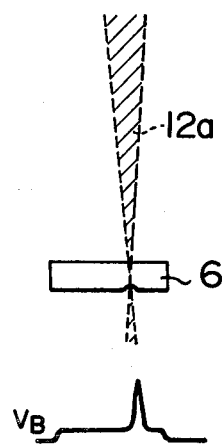

As a result, the spot diameters of the laser beams 13a and 12a on the front and rear surfaces of the sample 6 are different so that the resulting output signals v are different. When the defect exists on the front surface, the output signal $v_A$ is larger than the output signal $v_B$ at the position of the defect as shown in FIG. 31. When the defect exists on the rear surface, $v_B>v_A$ at the position of the defect, as shown in FIGS. 32A and 32B. By using the above nature, the defect bearing surface can be discriminated in a manner described below. In FIG. 32, (t) and (t+1) represent reflection periods by mirror planes t and t+1, respectively.

Figure 33:
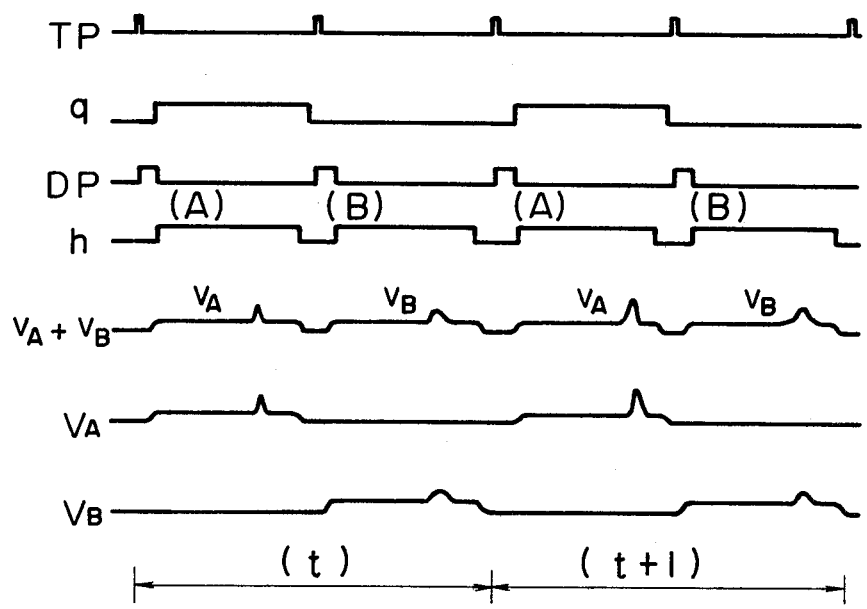
FIG. 33 shows a time chart for the separation of output signals by two laser beams.

FIG. 33 shows a timing chart for the signals. Since a return light detector 83 of FIG. 31 produces an ON output g only during the scan period by the laser beam 13a, the output signals $v_A$ and $v_B$ can be separated from the output $v(=v_A+v_B)$ of the photo-electric detector 10 by the output g.

Figure 34A:
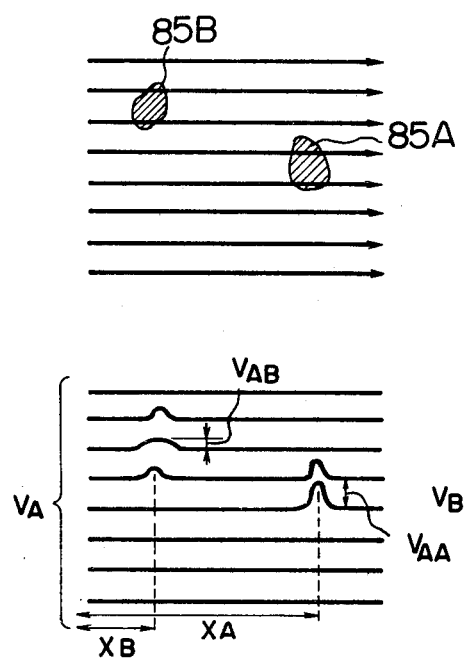
FIGS. 34A and 34B show output signals for a front surface defect and a rear surface defect.
Figure 34B:
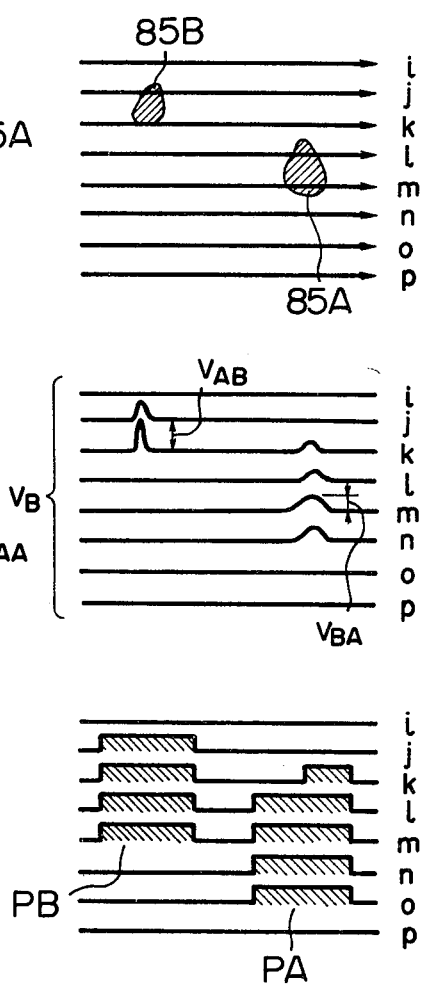

FIGS. 34A and 34B show the output signals $v_A$ and $v_B$ when a front surface defect 85A and a rear surface defect 85B exist. For the rear surface defect 85B, the laser beam 13a scans it with an apparently large spot size so that the output signal $v_A$ spreads widely and the maximum value $v_{AB}$ is small. The output signal $v_B$ resulting from the scan by the laser beam 13b having a smaller beam spot has a smaller spread and hence a larger maximum value $v_{BB}$. When the front surface defect 85A exists, the output signal $v_B$ by the laser beam 13b has a larger spread and hence $v_{AA}>v_{BA}$. Gate signals PA and PB are used commonly to the outputs $v_A$ and $v_B$, and as shown in FIGS. 34A and 34B the maximum values $v_{BB}$ and $v_{AA}$ of the outputs $v_B$ and $v_A$ and the corresponding positions are stored in the memory circuit at the timing of $x=x_B+a$, $y=\overline{m}$ for the defect 85B and $x=x_A+a$, $y=\overline{o}$ for the defect 85A.

FIG. 35 shows a configuration of an apparatus for the above operation. The m sets of maximum value memory circuits each including the maximum value memory circuits 80A and 80B are provided. A switcher 84 detects the return light output q shown in FIG. 31 to discriminate the laser beams 13a and 13b and supplies the separated output signals $v_A$ and $v_B$ to the maximum value memory circuits 80A and 80B. In the present arrangement, the maximum values $v_{AB}$ and $v_{AA}$ are produced from the first set of maximum value memory circuits 80A and 80B and the maximum values $v_{BB}$ and $v_{BA}$ are produced from the second set of maximum value memory circuits 80A and 80B. Those maximum values are compared by the memory circuit 78 within the same two-dimensional frame so that the rear surface defect 85B is detected from $v_{BB}$ and $v_{AB}$ and the front surface defect 85A is detected when $v_{AA} > v_{BA}$.

In order to discriminate the front and rear surface defects, it is necessary to compare the maximum values within each gate period (two-dimensional frame). If the two-dimensional frame (position) is not identified, a malfunction occurs because with respect to, for example, the defects 85B shown in FIGS. 34A and 34B $v_{BB}$ is larger than $v_{AB}$ for the scan lines j and k but the output by the laser beam 13a is larger for the scan line l. The present embodiment can avoid such malfunction.

As described hereinabove, according to the present invention, the number of defects on the plate and the sizes thereof can be exactly and automatically detected, and for the transparent plate the number of defects on the front and rear surfaces of the plate and the sizes thereof can be automatically detected.

What is claimed is:

1. A test apparatus for defects on a plate comprising:
   first surface irradiation means for irradiating and focusing a first illumination light to one surface of said plate;
   second surface irradiation means for irradiating and focusing a second illumination light to the other surface of said plate;
   scan means for scanning said one and the other surfaces of said plate by said first and second illumination lights;
   detection means for detecting scattered lights from said surfaces of said plate;
   a binary circuit for determining if a detection signal from said detection means exceeds a predetermined threshold;
   a plurality of two-dimensional frame setting means one for each of said first and second surface irradiation means for producing a gate signal of a predetermined width including an initial position on a scan line scanned by said scan means when said detection signal exceeds said threshold at said initial position and continuously producing said gate signal until said detection signal no longer exceeds said predetermined threshold within said width of said gate signal on the succeeding scan lines; and
   means for determining the numbers of the defects on said one surface and said other surface of said plate by the numbers of the two-dimensional frames set by said plurality of two-dimensional frame setting means.

2. A test apparatus for detects on a plate according to claim 1 wherein a plurality of said binary circuits having different thresholds are provided one for each of said first and second surface irradiation means.

3. A test apparatus for defects on a plate according to claim 2 further comprising maximum value detection means for detecting a maximum value of the detection signals within the two-dimensional frames set by said plurality of two-dimensional frame setting means whereby the sizes of the defects on said one surface and said other surface of said plate are determined.

4. A test apparatus for defects on a plate according to claim 1 or 2 further comprising switching means arranged between said detection means and said plurality of two-dimensional frame setting means for selectively supplying said detection signal from said detection means to selected one of said plurality of two-dimensional frame setting means depending on which one of said first and second surface irradiation means irradiates the light.

5. A test apparatus for defects on a plate according to claim 1, wherein said plate is a transparent plate, said one surface and said other surface of said plate are opposite surfaces of said plate, said second surface irradiation means is disposed on the same side as said scan means with respect to said transparent plate for focusing said second illumination light to said other surface of said transparent plate through said transparent plate, and said first and second illumination lights are first and second laser beams.

6. An apparatus for detecting defects on two opposite surfaces of a transparent plate comprising:
   generating means for generating at least two laser beams from different positions;
   a rotatable mirror for scanning in a predetermined direction each of said laser beams with a time interval corresponding to said different positions;
   scanning means for scanning at least one of said laser beams and said transparent plate in a direction substantially perpendicular to said predetermined direction;
   focusing means for focusing said one laser beam to one surface of said transparent plate and focusing said other laser beam to the other surface of said transparent plate, said focusing means being disposed on the same side as said rotatable mirror with respect to said transparent plate;
   photo-detector means for detecting light scattered from defects on said surfaces of said transparent plate;
   memory means for storing at least two image signals detected by said photo-detector means and corresponding to said laser beams scanned by said rotatable mirror; and
   means for comparing values of said image signals corresponding to identical positions on the surfaces as determined by said time interval of said image signals and for determining the larger value of the image signal at the position as an indication of which of the surfaces of said transparent plate has a defect.

7. An apparatus according to claim 6, wherein said plate has a comb-shaped pattern for causing light to be scattered in a given direction, and further comprising a light stopper for interrupting the light scattered in said direction from said pattern, whereby the light scattered from the defects on said one and said other surfaces of said plate are detected.

8. An apparatus according to claim 6, further comprising:
   a binary circuit for determining if an image signal from said photo-detector means exceeds a predetermined threshold;
   a plurality of two-dimensional frame setting means, one of said two-dimensional frame setting means provided for each of said laser beams and including means for producing a gate signal of a predetermined width having an initial position appearing as a defect signal on a scan line scanned by said rotatable mirror when said image signal exceeds said threshold at said initial position and continuouslt producing said gate signal until said image signal no longer exceeds said predetermined threshold within said width of said gate signal on the succeeding scan lines; and
   means for determining the number of defects on said surface of said transparent plate by the number of two-dimensional frames set by said two-dimensional frame setting means.

9. An apparatus according to claim 6, further including an aperture for stopping the focusing of said laser beams outside of the area to be detected of said transparent plate.

10. An apparatus for detecting defects on two opposite surfaces of a transparent plate comprising:
generating means for generating at least two laser beams from different positions;
scanning means for scanning in a predetermined direction each of said laser beams with a time interval corresponding to the different positions;
focusing means for focusing one of said laser beams to one surface of said transparent plate and focusing another of said laser beams to the other surface of said transparent plate by passing the another laser beam through said transparent plate, said focusing means being disposed on the same side as said scanning means with respect to said transparent plate;
photo-detector means for detecting light scattered from defects on said surfaces of said transparent plate and providing an output indicative thereof; and
defect determining means responsive to the output of said photo-detector means for determining which surface of the two opposing surfaces is provided with a defect.

11. An apparatus according to claim 10, wherein the output of said photo-detector means includes at least two image signals corresponding to the laser beams scanned by said scanning means, and said defect determining means includes memory means for storing said at least two image signals detected by said photo-detector means, means for comparing values of said image signals corresponding to identical positions on said surfaces of said transparent plate as determined by said time interval of said image signals and for determining the larger value of the image signal at the position as an indication of which surface of said transparent plate is provided with a defect.

12. An apparatus according to claim 11, wherein said memory means stores maximum values of the image signals corresponding to identical positions on the surfaces, and said comparing means compares the maximum value signals to determine the larger value.

13. An apparatus according to claim 12, wherein said plate has a comb-shaped pattern for causing light to be scattered in a given direction, and further comprising light stopping means for interrupting the light scattered in said direction from said pattern, whereby the light scattered from defects on the one and the another surface of said transparent plate are detected.

14. An apparatus according to claim 12, wherein said defect determining means further comprises binary circuit means for determining if an image signal from said photo-detector means exceeds a predetermined threshold, a plurality of two-dimensional frame setting means corresponding to the number of laser beams and comprising means for producing a gate signal of a predetermined width including an initial position appearing at a defect signal on a scan line scanned by said scanning means when said image signal exceeds said threshold at said initial position and continuously producing said gate signal until said image signal no longer exceeds said predetermined threshold within the width of said gate signal on the succeeding scanning lines, and means for determining the number of defects on the surface of said transparent plate by the number of two-dimensional frames set by said two-dimensional frame setting means.

15. An apparatus according to claim 12, further comprising means providing an aperture for stopping the focusing of laser beams outside of the area to be detected of said transparent plate.

* * * * *